United States Patent [19]
Pinkel et al.

[11] Patent Number: 5,830,645
[45] Date of Patent: Nov. 3, 1998

[54] COMPARATIVE FLUORESCENCE HYBRIDIZATION TO NUCLEIC ACID ARRAYS

[75] Inventors: Daniel Pinkel, Walnut Creek, Calif.; Donna Albertson, Cambridge, United Kingdom; Joe W. Gray, San Francisco, Calif.

[73] Assignees: The Regents of the University of California, Oakland, Calif.; The Medical Research Council, Cambridge, England

[21] Appl. No.: 353,018

[22] Filed: Dec. 9, 1994

[51] Int. Cl.[6] .............................. C12W 1/68; C12P 19/34; C07H 21/04
[52] U.S. Cl. ........................... 435/6; 435/91.2; 536/24.3; 536/24.33; 536/26.6; 382/128; 382/129
[58] Field of Search .................. 435/6, 91.2; 427/213.1; 382/128, 129; 536/24.3, 24.33, 26.6

[56] References Cited

U.S. PATENT DOCUMENTS

| | | | |
|---|---|---|---|
| 4,981,783 | 1/1991 | Augenlicht et al. | 435/6 |
| 5,028,525 | 7/1991 | Gray et al. | 435/6 |
| 5,173,260 | 12/1992 | Zander et al. | 422/57 |
| 5,194,300 | 3/1993 | Cheung et al. | 427/213.31 |
| 5,447,841 | 9/1995 | Gray et al. | 435/6 |

FOREIGN PATENT DOCUMENTS

| | | | |
|---|---|---|---|
| WO 93/18186 | 9/1993 | WIPO | C12Q 1/68 |
| WO 95/35505 | 12/1995 | WIPO | 33/543 |

OTHER PUBLICATIONS

Gray et al, Molecular Cytogenetics, diagnosis and prognosis assessment, Current Opin Biotech. 3(6) 623–31., 1992.
Kallioniemi, Comparative Genomic Hybridization for Molecular Cytogenetic Analysis of Solid Tumors, Science 258, 818–821, 1992.
Joos et al, Mopping and chromosome analysis; one potential of fluorescence in situ hybridization, J. of Biotechnology 35:135–153, 1994.
Southern, EM et al, Analyzing and Comparing Nucleic Acid Sequence by hybridization Arrays of Oligonucleotides; Evaluation using experimental models, Genomics 13:1008–1017.
Hoeltke et al. Analytical Biochemistry 207:24–31, 1992.
Bauwens et al. Plant Journal, 6: 123–131, 1993.
Nizetic et al. PNAS 88:3233–3237, 1991.
Phillips et al., Proc Annu Meet. Am Assoc. Cancer Research, 35:A3450 Abstract, 1994.
Zucman, et al., "Rapid Isolution of Cosmids from Defined Subregions by Differential Alu–PCR Hybridization on Chromosome 22–Specific Library," *Genomics* 13:395–401 (1992).
Chumakov, et al., "Isolation of chromosome 21–specific yeast artificial chromosomes from a total human genome library," *Nature Genetics* 1:222–225 (1992).
Ross, et al., "Selection of a human chromosome 21 enriched YAC sub–library using a chromosome–specific composite probe," *Nature Genetics* 1:284–290 (1992).
WO 95/18235 (PCT/EP94/04208, filed Dec.17, 1994) Published Jul. 6, 1995 Cremer, et al.

*Primary Examiner*—W. Gary Jones
*Assistant Examiner*—Dianne Rees
*Attorney, Agent, or Firm*—Townsend and Townsend and Crew

[57] ABSTRACT

The present invention provides methods of determining relative copy number of target nucleic acids and precise mapping of chromosomal abnormalities associated with disease. The methods of the invention use target nucleic acids immobilized on a solid surface, to which a sample comprising two sets of differentially labeled nucleic acids are hybridized. The hybridization of the labeled nucleic acids to the solid surface is then detected using standard techniques.

16 Claims, 1 Drawing Sheet

COMPARATIVE FLUORESCENCE HYBRIDIZATION TO NUCLEIC ACID ARRAYS

The Government has rights in this invention pursuant to and Grant No. CA-45919 by the National Institutes of Health.

BACKGROUND OF THE INVENTION

The present invention relates to methods for detecting and mapping genetic abnormalities associated with various diseases. In particular, it relates to the use of nucleic acid hybridization methods for comparing copy numbers of particular nucleic acid sequences in a collection of sequences relative to the copy number of these sequences in other collections of sequences.

Many genomic and genetic studies are directed to the identification of differences in gene dosage or expression among cell populations for the study and detection of disease. For example, many malignancies involve the gain or loss of DNA sequences resulting in activation of oncogenes or inactivation of tumor suppressor genes. Identification of the genetic events leading to neoplastic transformation and subsequent progression can facilitate efforts to define the biological basis for disease, improve prognostication of therapeutic response, and permit earlier tumor detection.

In addition, perinatal genetic problems frequently result from loss or gain of chromosome segments such as trisomy 21 or the micro deletion syndromes. Thus, methods of prenatal detection of such abnormalities can be helpful in early diagnosis of disease.

Cytogenetics is the traditional method for detecting amplified or deleted chromosomal regions. The resolution of cytogenetic techniques is limited, however, to regions larger than approximately 10 Mb (approximately the width of a band in Giemsa-stained chromosomes). In complex karyotypes with multiple translocations and other genetic changes, traditional cytogenetic analysis is of little utility because karyotype information cannot be fully interpreted. Furthermore conventional cytogenetic banding analysis is time consuming, labor intensive, and frequently difficult or impossible due to difficulties in obtaining adequate metaphase chromosomes. In addition, the cytogenetic signatures of gene amplification, homogeneously staining regions (HSR), or double minute chromosomes, do not provide any information that contributes to the identification of the sequences that are amplified.

More recent methods permit assessing the amount of a given nucleic acid sequence in a sample using molecular techniques. These methods (e.g., Southern blotting) employ cloned DNA or RNA probes that are hybridized to isolated DNA. Southern blotting and related techniques are effective even if the genome is heavily rearranged so as to eliminate useful karyotype information. However, these methods require use of a probe specific for the sequence to be analyzed. Thus, it is necessary to employ very many individual probes, one at a time, to survey the entire genome of each specimen, if no prior information on particular suspect regions of the genome is available.

Comparative genomic hybridization (CGH) is a more recent approach to detect the presence and identify the location of amplified or deleted sequences. See, Kallioniemi et al., Science 258:818–821 (1992) and WO 93/18186). CGH reveals increases and decreases irrespective of genome rearrangement. In one implementation of CGH, genomic DNA is isolated from normal reference cells, as well as from test cells (e.g., tumor cells). The two nucleic acids are differentially labelled and then hybridized in situ to metaphase chromosomes of a reference cell. The repetitive sequences in both the reference and test DNAs are either removed or their hybridization capacity is reduced by some means. Chromosomal regions in the test cells which are at increased or decreased copy number can be quickly identified by detecting regions where the ratio of signal from the two DNAs is altered. For example, those regions that have been decreased in copy number in the test cells will show relatively lower signal from the test DNA than the reference compared to other regions of the genome. Regions that have been increased in copy number in the test cells will show relatively higher signal from the test DNA.

Thus, CGH discovers and maps the location of the sequences with variant copy number without prior knowledge of the sequences. No probes for specific sequences are required and only a single hybridization is required. Where a decrease or an increase in copy number is limited to the loss or gain of one copy of a sequence, the CGH resolution is usually about 5–10 Mb.

New techniques which provide increased sensitivity, more precise localization of chromosomal abnormalities and which can detect differences in levels of gene expression are particularly desirable for the diagnosis of disease. The present invention provides these and other benefits.

SUMMARY OF THE INVENTION

The present invention provides methods for quantitatively comparing copy numbers of at least two nucleic acid sequences in a first collection of nucleic acid molecules relative to the copy numbers of those same sequences in a second collection. The method comprises labeling the nucleic acid molecules in the first collection and the nucleic acid molecules in the second collection with first and second labels, respectively. The first and second labels should be distinguishable from each other. The probes thus formed are contacted to a plurality of target elements under conditions such that nucleic acid hybridization to the target elements can occur. The probes can be contacted to the target elements either simultaneously or serially.

Each target element comprises target nucleic acid molecules bound to a solid support. One or more copies of each sequence in a target element may be present. The sequence complexity of the target nucleic acids in the target element are much less than the sequence complexity of the first and second collections of labeled nucleic acids.

The nucleic acids for both the target elements and the probes may be, for example, RNA, DNA, or cDNA. The nucleic acids may be derived from any organism. Usually the nucleic acid in the target elements and the probes are from the same species.

The target elements may be on separate supports, such as a plurality of beads, or an array of target elements may be on a single solid surface, such as a glass microscope slide. The nucleic acid sequences of the target nucleic acids in a target element are those for which comparative copy number information is desired. For example, the sequence of an element may originate from a chromosomal location known to be associated with disease, may be selected to be representative of a chromosomal region whose association with disease is to be tested, or may correspond to genes whose transcription is to be assayed.

After contacting the probes to the target elements the amount of binding of each, and the binding ratio is determined for each target element. Typically the greater the ratio of the binding to a target element the greater the copy number ratio of sequences in the two probes that bind to that element. Thus comparison of the ratios among target elements permits comparison of copy number ratios of different sequences in the probes.

The methods are typically carried out using techniques suitable for fluorescence in situ hybridization. Thus, the first and second labels are usually fluorescent labels.

To inhibit hybridization of repetitive sequences in the probes to the target nucleic acids, unlabeled blocking nucleic acids (e.g., Cot-1 DNA) can be mixed with the probes. Thus, the invention focuses on the analysis of the non-repetitive sequences in a genome.

In a typical embodiment, one collection of probe nucleic acids is prepared from a test cell, cell population, or tissue under study; and the second collection of probe nucleic acids is prepared from a reference cell, cell population, or tissue. Reference cells can be normal non-diseased cells, or they can be from a sample of diseased tissue that serves as a standard for other aspects of the disease. For example, if the reference probe is genomic DNA isolated from normal cells, then the copy number of each sequence in that probe relative to the others is known (e.g., two copies of each autosomal sequence, and one or two copies of each sex chromosomal sequence depending on gender). Comparison of this to a test probe permits detection in variations from normal. Alternatively the reference probe may be prepared from genomic DNA from a primary tumor which may contain substantial variations in copy number among its different sequences, and the test probe may prepared from genomic DNA of metastatic cells from that tumor, so that the comparison shows the differences between the primary tumor and its metastasis. Further, both probes may be prepared from normal cells. For example comparison of mRNA populations between normal cells of different tissues permits detection of differential gene expression that is a critical feature of tissue differentiation. Thus in general the terms test and reference are used for convenience to distinguish the two probes, but they do not imply other characteristics of the nucleic acids they contain.

The invention also provides kits comprising materials useful for carrying out the methods of the invention. Kits of the invention comprise a solid support having an array of target nucleic acids bound thereto and a container containing nucleic acids representing a normal reference genome, or cDNA from a reference cell type, and the like. The kit may further comprise two different fluorochromes, reagents for labeling the test genomes, alternate reference genomes and the like.

Definitions

A "nucleic acid array" is a plurality of target elements, each comprising one or more target nucleic acid molecules immobilized on a solid surface to which probe nucleic acids are hybridized.

"Target nucleic acids" of a target element typically have their origin in a defined region of the genome (for example a clone or several contiguous clones from a genomic library), or correspond to a functional genetic unit, which may or may not be complete (for example a full or partial cDNA). The target nucleic acids can also comprise inter-Alu or Degenerate Oligonucleotide Primer PCR products derived from such clones. If gene expression is being analyzed, a target element can comprise a full or partial cDNA.

The target nucleic acids of a target element may, for example, contain specific genes or, be from a chromosomal region suspected of being present at increased or decreased copy number in cells of interest, e.g., tumor cells. The target element may also contain an mRNA, or cDNA derived from such mRNA, suspected of being transcribed at abnormal levels.

Alternatively, a target element may comprise nucleic acids of unknown significance or location. An array of such elements could represent locations that sample, either continuously or at discrete points, any desired portion of a genome, including, but not limited to, an entire genome, a single chromosome, or a portion of a chromosome. The number of target elements and the complexity of the nucleic acids in each would determine the density of sampling. For example an array of 300 target elements, each target containing DNA from a different genomic clone, could sample the entire human genome at 10 megabase intervals. An array of 30,000 elements, each containing 100 kb of genomic DNA could give complete coverage of the human genome.

Similarly, an array of targets elements comprising nucleic acids from anonymous cDNA clones would permit identification of those that might be differentially expressed in some cells of interest, thereby focusing attention on study of these genes.

Target elements of various dimensions can be used in the arrays of the invention. Generally, smaller, target elements are preferred. Typically, a target element will be less than about 1 cm in diameter. Generally element sizes are from 1 $\mu$m to about 3mm, preferably between about 5 $\mu$m and about 1 mm.

The target elements of the arrays may be arranged on the solid surface at different densities. The target element densities will depend upon a number of factors, such as the nature of the label, the solid support, and the like.

One of skill will recognize that each target element may comprise a mixture of target nucleic acids of different lengths and sequences. Thus, for example, a target element may contain more than one copy of a cloned piece of DNA, and each copy may be broken into fragments of different lengths. The length and complexity of the target sequences of the invention is not critical to the invention. One of skill can adjust these factors to provide optimum hybridization and signal production for a given hybridization procedure, and to provide the required resolution among different genes or genomic locations. Typically, the target sequences will have a complexity between about 1 kb and about 1 Mb.

In preferred embodiments, the targets of the invention are nucleic acids which substantially lack superstructure associated with condensed metaphase chromosomes from which they are derived. The general nature of the packing of DNA into eukaryotic chromosomes is well known to those of skill in the art. Briefly, the superstructure of a eukaryotic chromosome comprises many orders of complexity. DNA is wrapped around a histone core to form regular repeating nucleosomes, which, in turn, are packed one upon another to generate more tightly condensed 30 nm chromatin fibers. The chromatin fibers are then further packed in a variety of looped domains to produce higher orders of folding and condensation in the metaphase chromosome. The nucleic acid targets of the invention lack some or all of the these features of naturally occurring condensed, metaphase chromosomes. For a general description of global structure of eukaryotic chromosomes, see, Alberts et al. *Molecular Biology of the Cell* 2nd ed. pp 496–506, Garland Publishing Inc. New York, 1989).

The terms "nucleic acid" or "nucleic acid molecule" refer to a deoxyribonucleotide or ribonucleotide polymer in either single- or double-stranded form, and unless otherwise limited, would encompass known analogs of natural nucleotides that can function in a similar manner as naturally occurring nucleotides.

As used herein a "probe" is defined as a collection of nucleic acid molecules (either RNA or DNA) capable of binding to a target nucleic acid of complementary sequence through one or more types of chemical bonds, usually through hydrogen bond formation. The probes are preferably directly or indirectly labelled as described below. They are typically of high complexity, for instance, being prepared from total genomic DNA or mRNA isolated from a cell or cell population.

The term "complexity" is used here according to standard meaning of this term as established by Britten et al. *Methods of Enzymol.* 29:363 (1974). See, also Cantor and Schimmel *Biophysical Chemistry: Part III* at 1228–1230 for further explanation of nucleic acid complexity.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The terms "specific hybridization" or "specifically hybridizes with" refers to hybridization in which a probe nucleic acid binds substantially to target nucleic acid and does not bind substantially to other nucleic acids in the array under defined stringency conditions. One of skill will recognize that relaxing the stringency of the hybridizing conditions will allow sequence mismatches to be tolerated. The degree of mismatch tolerated can be controlled by suitable adjustment of the hybridization conditions.

One of skill will also recognize that the precise sequence of the particular nucleic acids described herein can be modified to a certain degree to produce probes or targets that are "substantially identical" to others, and retain the ability to bind substantially to a complementary nucleic acid. Such modifications are specifically covered by reference to individual sequences herein. The term "substantial identity" of polynucleotide sequences means that a polynucleotide comprises a sequence that has at least 90% sequence identity, and more preferably at least 95%, compared to a reference sequence using the methods described below using standard parameters.

Two nucleic acid sequences are said to be "identical" if the sequence of nucleotides in the two sequences is the same when aligned for maximum correspondence as described below. The term "complementary to" is used herein to mean that the complementary sequence is complementary to all or a portion of a reference polynucleotide sequence.

Sequence comparisons between two (or more) polynucleotides are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85:2444 (1988), by computerized implementations of these algorithms.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

Another indication that nucleotide sequences are substantially identical is if two molecules hybridize to the same sequence under stringent conditions. Stringent conditions are sequence dependent and will be different in different circumstances. Generally, stringent conditions are selected to be about 50° C. lower than the thermal melting point (Tm) for the specific sequence at a defined ionic strength and pH. The Tm is the temperature (under defined ionic strength and pH) at which 50% of the target sequence hybridizes to a perfectly matched probe.

DESCRIPTION OF THE PREFERRED EMBODIMENTS

Figure 1:
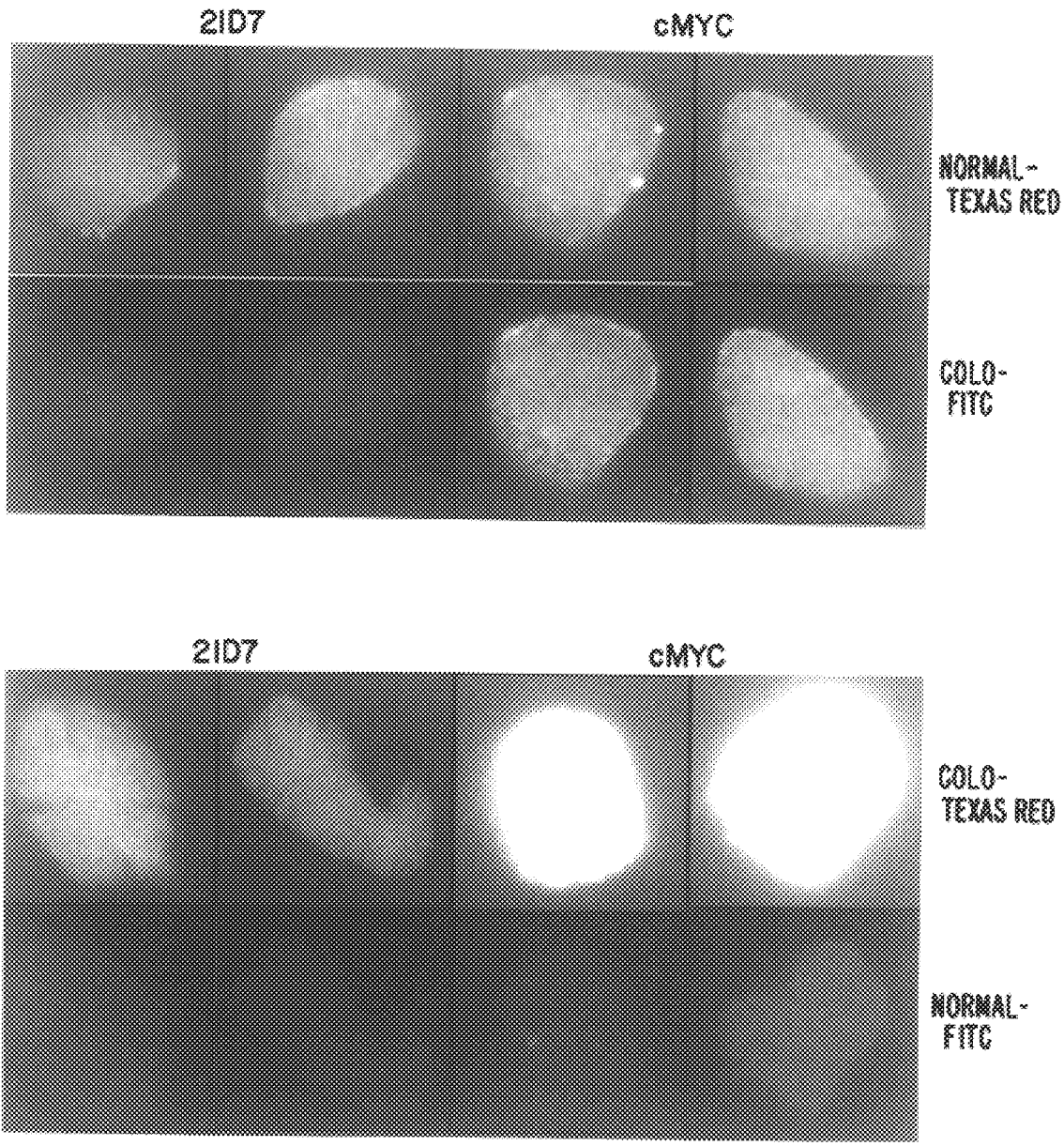
FIG. 1 shows photomicrographs of experiments showing the ability of the methods of the invention to detect an amplification of the cMYC oncogene. Labelled Colo-320 DNA, which contains an amplification of the cMYC oncogene, and labelled normal human DNA were hybridized to an array consisting of two target elements. One target element contained cloned cMYC oncogene sequences, and the other contained cloned sequences from a region of the human genome (21D7) known to be unamplified in the Colo-320 cell line. Each target element comprises single stranded fragments corresponding to a clone. The fragments were immobilized on avidin coated glass particles.

The present invention provides methods for comparing abnormal nucleic acid copy number and mapping of chromosomal abnormalities associated with disease. The methods of the invention use target nucleic acids immobilized on a solid support, to which differentially labeled probe nucleic acids are hybridized. The hybridization of the labeled nucleic acids to the target is then detected using standard techniques.

The methods of the invention compare the copy numbers of sequences capable of binding to the target elements. Variations in copy number detectable by the methods of the invention may arise in different ways. For example, copy number may be altered as a result of amplification or deletion of a chromosomal region. Alternatively, copy number may be reduced by genetic rearrangements that alter the sequences in the probe or target nucleic acids sufficiently to reduce their binding.

Target Nucleic Acids

Target nucleic acids of the invention can be derived from virtually any source. Typically, the targets will be nucleic acid molecules derived from representative locations along a chromosome of interest, a chromosomal region of interest, an entire genome of interest, a cDNA library, and the like. These target nucleic acids may be relatively long (typically thousands of bases) fragments of nucleic acid obtained from, for instance, inter-Alu PCR products of genomic clones, restriction digests of genomic clone, cDNA clones and the like. In some embodiments the target nucleic acids are a previously mapped library of clones spanning a particular region of interest.

The choice of target nucleic acids to use may be influenced by prior knowledge of the association of a particular chromosome or chromosomal region with certain disease conditions. International Application WO 93/18186, supra, provides a list of chromosomal abnormalities and associated diseases, which are described in the scientific literature. Alternatively, whole genome screening to identify new region subject to frequent changes in copy number can be performed using the methods of the present invention. In these embodiments, target elements usually contain nucleic acids representative of locations distributed over the entire genome. In some embodiments (e.g., using a large number of target elements of high complexity) all sequences in the genome can be present in the array.

In some embodiments, previously mapped clones from a particular chromosomal region of interest are used as targets. Such clones are becoming available as a result of rapid progress of the worldwide initiative in genomics.

Mapped clones can be prepared from libraries constructed from single chromosomes, multiple chromosomes, or from a segment of a chromosome. Standard techniques are used to clone suitably sized fragments in vectors such as cosmids, yeast artificial chromosomes (YACs), bacterial artificial chromosomes (BACs) and P1 phage.

While it is possible to generate clone libraries, as described above, libraries spanning entire chromosomes are also available commercially. For instance, chromosome-specific libraries from the human and other genomes are available for Clonetech (South San Francisco, Calif.) or from The American Type Culture Collection (see, *ATCC/NIH Repository of Catalogue of Human and Mouse DNA Probes and Libraries,* 7th ed. 1993).

If necessary, clones described above may be genetically or physically mapped. For instance, FISH and digital image analysis can be used to localize cosmids along the desired chromosome. This method is described, for instance, in Lichter et al., *Science,* 247:64–69 (1990). The physically mapped clones can then be used to more finally map a region of interest identified using CGH or other methods.

Attachment of Target Nucleic Acids to a Solid Surface

Many methods for immobilizing nucleic acids on a variety of solid surfaces are known in the art. For instance, the solid surface may be a membrane, glass, plastic, or a bead. The desired component may be covalently bound or non-covalently attached through nonspecific binding. The immobilization of nucleic acids on solid surfaces is discussed more fully below.

A wide variety of organic and inorganic polymers, as well as other materials, both natural and synthetic, may be employed as the material for the solid surface. Illustrative solid surfaces include nitrocellulose, nylon, glass, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition substances that form gels can be used. Such materials include proteins (e.g., gelatins), lipopolysaccharides, silicates, agarose and polyacrylamides. Where the solid surface is porous, various pore sizes may be employed depending upon the nature of the system.

In preparing the surface, a plurality of different materials may be employed, particularly as laminates, to obtain various properties. For example, proteins (e.g., bovine serum albumin) or mixtures of macromolecules (e.g., Denhardt's solution) can be employed to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. For example, methods for immobilizing nucleic acids by introduction of various functional groups to the molecules is known (see, e.g., Bischoff et al., *Anal. Biochem.* 164:336–344 (1987); Kremsky et al., *Nuc. Acids Res.* 15:2891–2910 (1987)). Modified nucleotides can be placed on the target using PCR primers containing the modified nucleotide, or by enzymatic end labeling with modified nucleotides.

Use of membrane supports (e.g., nitrocellulose, nylon, polypropylene) for the nucleic acid arrays of the invention is advantageous because of well developed technology employing manual and robotic methods of arraying targets at relatively high element densities (e.g., up to 30–40/cm$^2$). In addition, such membranes are generally available and protocols and equipment for hybridization to membranes is well known. Many membrane materials, however, have considerable fluorescence emission, where fluorescent labels are used to detect hybridization.

To optimize a given assay format one of skill can determine sensitivity of fluorescence detection for different combinations of membrane type, fluorochrome, excitation and emission bands, spot size and the like. In addition, low fluorescence background membranes have been described (see, e.g., Chu et al., *Electrophoresis* 13:105–114 (1992)).

The sensitivity for detection of spots of various diameters on the candidate membranes can be readily determined by, for example, spotting a dilution series of fluorescently end labeled DNA fragments. These spots are then imaged using conventional fluorescence microscopy. The sensitivity, linearity, and dynamic range achievable from the various combinations of fluorochrome and membranes can thus be determined. Serial dilutions of pairs of fluorochrome in known relative proportions can also be analyzed to determine the accuracy with which fluorescence ratio measurements reflect actual fluorochrome ratios over the dynamic range permitted by the detectors and membrane fluorescence.

Arrays on substrates with much lower fluorescence than membranes, such as glass, quartz, or small beads, can achieve much better sensitivity. For example, elements of various sizes, ranging from the ~1 mm diameter down to ~1 $\mu$m can be used with these materials. Small array members containing small amounts of concentrated target DNA are conveniently used for high complexity comparative hybridizations since the total amount of probe available for binding to each element will be limited. Thus it is advantageous to have small array members that contain a small amount of concentrated target DNA so that the signal that is obtained is highly localized and bright. Such small array members are typically used in arrays with densities greater than 10$^4$/cm$^2$. Relatively simple approaches capable of quantitative fluorescent imaging of 1 cm$^2$ areas have been described that permit acquisition of data from a large number of members in a single image (see, e.g., Wittrup et. al. *Cytometry* 16:206–213 (1994)).

Covalent attachment of the target nucleic acids to glass or synthetic fused silica can be accomplished according to a number of known techniques. Such substrates provide a very low fluorescence substrate, and a highly efficient hybridization environment.

There are many possible approaches to coupling nucleic acids to glass that employ commercially available reagents. For instance, materials for preparation of silanized glass with a number of functional groups are commercially available or can be prepared using standard techniques. Alternatively, quartz cover slips, which have at least 10-fold lower auto fluorescence than glass, can be silanized.

The targets can also be immobilized on commercially available coated beads or other surfaces. For instance, biotin end-labelled nucleic acids can be bound to commercially available avidin-coated beads. Streptavidin or anti-digoxigenin antibody can also be attached to silanized glass slides by protein-mediated coupling using e.g., protein A following standard protocols (see, e.g., Smith et al. Science, 258:1122–1126 (1992)). Biotin or digoxigenin end-labeled nucleic acids can be prepared according to standard techniques.

Hybridization to nucleic acids attached to beads is accomplished by suspending them in the hybridization mix, and then depositing them on the glass substrate for analysis after washing. Alternatively, paramagnetic particles, such as ferric oxide particles, with or without avidin coating, can be used.

The prior art also describes techniques capable of producing high density arrays for various applications including sequencing by hybridization and detection of particular sequences (see, e.g., Fodor et al. Science 767–773 (1991) and U.S. Pat. No. 5,143,854).

Preparation of Probe Nucleic Acids

As with target nucleic acids, a wide variety of nucleic acids can be used as probe nucleic acids in the methods of the present invention. The probes may be comprise, for example, genomic DNA representing the entire genome from a particular organism, tissue or cell type or may comprise a portion of the genome, such as a single chromosome.

To compare expression levels of a particular gene or genes, the probes nucleic acids can be derived from mRNA or cDNA prepared from an organism, tissue, or cell of interest. For instance, test cDNA or mRNA, along with mRNA or cDNA from normal reference cells, can be hybridized to an array of clones from a normalized cDNA library. In addition, probes made from genomic DNA from two cell populations can be hybridized to a cDNA array to detect those cDNAs that come from regions of variant DNA copy number in the genome.

The methods of the invention are suitable for comparing copy number of particular sequences in any combination of two or more populations of nucleic acids. One of skill will recognize that the particular populations of sample nucleic acids being compared is not critical to the invention. For instance, genomic or cDNA can be compared from two related species. Alternatively, levels of expression of particular genes in two or more tissue or cell types can be compared. As noted above, the methods are particularly useful in the diagnosis of disease.

Standard procedures can be used to isolate nucleic acids (either DNA or mRNA) from appropriate tissues (see, e.g., Sambrook, et al., Molecular Cloning—A Laboratory Manual, Cold Spring Harbor Laboratory, Cold Spring Harbor, N.Y. (1985)). Conventional methods for preparation of cDNA from mRNA can also be used.

The particular cells or tissue from which the nucleic acids are isolated will depend upon the particular application. Typically, for detection of abnormalities associated with cancer, genomic DNA is isolated from tumor cells. For prenatal detection of disease, fetal tissue will be used.

If the tissue sample is small, so that a small amount of nucleic acids is available, amplification techniques such as the polymerase chain reaction (PCR) using degenerate primers can be used. For a general description of PCR, see, PCR Protocols, Innis et al. eds. Academic Press, 1990. In addition, PCR can be used to selectively amplify sequences between high copy repetitive sequences. These methods use primers complementary to highly repetitive interspersed sequences (e.g., Alu) to selectively amplify sequences that are between two members of the Alu family (see, Nelson et al., Proc. Natl. Acad. Sci. USA 86:6686 (1989)).

As noted above, CGH at the cytogenetic level is facilitating the search for disease genes by identifying regions of differences in copy number between a normal and tumor genome, for example. For instance, CGH studies have been applied to the analysis of copy number variation in breast cancer (see, e.g., Kallioniemi et al. Proc. Natl. Acad. Sci. USA 91:2156–2160 (1994)).

In CGH, the resolution with which a copy number change can be mapped is on the order of several megabases. With the present invention the resolution is a function of the length of the genomic DNA segments in the target elements and the difference in map position between neighboring clones. Resolution of more than a factor of 10 better than with standard CGH can be achieved with the present invention. This improved localization will facilitate efforts to identify the critical genes involved in a disease, and permit more sensitive detection of abnormalities involving a small region of the genome, such as in microdeletion syndromes.

Labelling Nucleic Acid Probes

As noted above, the nucleic acids which are hybridized to the target nucleic acids are preferably labelled to allow detection of hybridization complexes. The nucleic acid probes used in the hybridization described below may be detectably labeled prior to the hybridization reaction. Alternatively, a detectable label may be selected which binds to the hybridization product. As noted above, the target nucleic acid array is hybridized to two or more probe nucleic acids, either simultaneously or serially. Thus, the probes are each labeled with a separate and distinguishable label.

The particular label or detectable group attached to the probe nucleic acids is not a critical aspect of the invention, so long as it does not significantly interfere with the hybridization of the probe to the target sequence. The detectable group can be any material having a detectable physical or chemical property. Such detectable labels have been well-developed in the field of nucleic acid hybridizations and in general most any label useful in such methods can be applied to the present invention. Thus a label is any composition detectable by spectroscopic, photochemical, biochemical, immunochemical, electrical, optical or chemical means. Useful labels in the present invention include fluorescent dyes (e.g., fluorescein isothiocyanate, texas red, rhodamine, and the like) radiolabels (e.g., $^3$H, $^{125}$I, $^{35}$S, $^{14}$C, or $^{32}$P), enzymes (e.g., horse radish peroxidase, alkaline phosphatase and others commonly used in an ELISA).

The nucleic acids can be indirectly labeled using ligands for which detectable anti-ligands are available. For example, biotinylated nucleic acids can be detected using labeled avidin or streptavidin according to techniques well known in the art. In addition, antigenic or haptenic molecules can be detected using labeled antisera or monoclonal antibodies.

For example, N-acetoxy-N-2-acetylaminofluorene-labelled or digoxigenin-labelled probes can be detected using antibodies specifically immunoreactive with these compounds (e.g., FITC-labeled sheep anti-digoxigenin antibody (Boehringer Mannheim)). In addition, labeled antibodies to thymidine-thymidine dimers can be used (Nakane et al. *ACTA Histochem. Cytochem.* 20:229 (1987)).

Generally, labels which are detectable in as low a copy number as possible, thereby maximizing the sensitivity of the assay, and yet be detectable above any background signal are preferred. A label is preferably chosen that provides a localized signal, thereby providing spatial resolution of the signal from each target element.

The labels may be coupled to the DNA in a variety of means known to those of skill in the art. In a preferred embodiment the probe will be labeled using nick translation or random primer extension (Rigby, et al. *J. Mol. Biol.*, 113:237 (1977) or Sambrook, et al., *Molecular Cloning—A Laboratory Manual,* Cold Spring Harbor Laboratory, Cold Spring Harbor, N.Y. (1985)).

Hybridization of Labeled Nucleic Acids to Targets

The copy number of particular nucleic acid sequences in two probes are compared by hybridizing the probes to one or more target nucleic acid arrays. The hybridization signal intensity, and the ratio of intensities, produced by the probes on each of the target elements is determined. Typically the greater the ratio of the signal intensities on a target element the greater the copy number ratio of sequences in the two probes that bind to that element. Thus comparison of the signal intensity ratios among target elements permits comparison of copy number ratios of different sequences in the probes.

Standard hybridization techniques are used to probe a target nucleic acid array. Suitable methods are described in references describing CGH techniques (Kallioniemi et al., *Science* 258:818–821 (1992) and WO 93/18186). Several guides to general techniques are available, e.g., Tijssen, *Hybridization with Nucleic Acid Probes,* Parts I and II (Elsevier, Amsterdam 1993). For a descriptions of techniques suitable for in situ hybridizations see, Gall et al. *Meth. Enzymol.,* 21:470–480 (1981) and Angerer et al. in *Genetic Engineering: Principles and Methods* Setlow and Hollaender, Eds. Vol 7, pgs 43–65 (plenum Press, New York 1985).

Generally, nucleic acid hybridizations comprise the following major steps: (1) immobilization of target nucleic acids; (2) prehybridization treatment to increase accessibility of target DNA, and to reduce nonspecific binding; (3) hybridization of the mixture of nucleic acids to the nucleic acid on the solid surface; (4) posthybridization washes to remove nucleic acid fragments not bound in the hybridization and (5) detection of the hybridized nucleic acid fragments. The reagent used in each of these steps and their conditions for use vary depending on the particular application.

In some applications it is necessary to block the hybridization capacity of repetitive sequences. A number of methods for removing and/or disabling the hybridization capacity of repetitive sequences are known (see, e.g., WO 93/18186).

For instance, bulk procedures can be used. In many genomes, including the human genome, a major portion of shared repetitive DNA is contained within a few families of highly repeated sequences such as Alu. These methods exploit the fact that hybridization rate of complementary sequences increases as their concentration increases. Thus, repetitive sequences, which are generally present at high concentration will become double stranded more rapidly than others following denaturation and incubation under hybridization conditions. The double stranded nucleic acids are then removed and the remainder used in hybridizations. Methods of separating single from double stranded sequences include using hydroxyapatite or immobilized complementary nucleic acids attached to a solid support. Alternatively, the partially hybridized mixture can be used and the double stranded sequences will be unable to hybridize to the target.

Alternatively, unlabeled sequences which are complementary to the sequences whose hybridization capacity is to be inhibited can be added to the hybridization mixture. This method can be used to inhibit hybridization of repetitive sequences as well as other sequences. For instance, "Cot-1" DNA can be used to selectively inhibit hybridization of repetitive sequences in a sample. To prepare Cot-1 DNA, DNA is extracted, sheared, denatured and renatured to a $C_0t$~1 (for description of reassociation kinetics and $C_0t$ values, see, Tijssen, *supra* at pp 48–54). Because highly repetitive sequences reanneal more quickly, the resulting hybrids are highly enriched for these sequences. The remaining single stranded (i.e., single copy sequences) is digested with S1 nuclease and the double stranded Cot-1 DNA is purified and used to block hybridization of repetitive sequences in a sample. Although Cot-1 DNA can be prepared as described above, it is also commercially available (BRL).

Analysis of Detectable Signals from Hybridizations

Standard methods for detection and analysis of signals generated by labeled probes can be used. The particular methods will depend upon the labels used in the probes. Generally, fluorescent labels are preferred. Thus, methods suitable in fluorescence in situ hybridization (FISH) are suitable in the present invention. The nucleic acid arrays are imaged in a fluorescence microscope with a polychromatic beam-splitter to avoid color-dependent image shifts. The different color images are acquired with a CCD camera and the digitized images are stored in a computer. A computer program is then used to analyze the signals produced by the array.

Preferred methods of visualizing signals are described in Kallioniemi et al., *supra* and in WO 93/18186. To facilitate the display of results and to improve the sensitivity of detecting small differences in fluorescence intensity, a digital image analysis system is preferably used. A preferred system is QUIPS (an acronym for quantitative image processing system), which is an automated image analysis system based on a standard fluorescence microscope equipped with an automated stage, focus control and filterwheel (Ludl Electronic Products, Ltd., Hawthorne, N.Y.). The filterwheel is mounted in the fluorescence excitation path of the microscope for selection of the excitation wavelength. Special filters (Chroma Technology, Brattleboro, Vt.) in the dichroic block allow excitation of the multiple dyes without image registration shift. The microscope has two camera ports, one of which has an intensified CCD camera (Quantex Corp., Sunnyvale, Calif.) for sensitive high-speed video image display which is used for finding interesting areas on a slide as well as for focusing. The other camera port has a cooled CCD camera (model 200 by Photometrics Ltd., Tucson, Ariz.) which is used for the actual image acquisition at high resolution and sensitivity.

The cooled CCD camera is interfaced to a SUN 4/330 workstation (SUN Microsystems, Inc., Mountain View, Calif.) through a VME bus. The entire acquisition of multicolor images is controlled using an image processing software package SCIL-Image (Delft Centre for Image Processing, Delft, Netherlands).

EXAMPLE 1

This example demonstrates detection of the amplification of a specific sequence in a tumor cell line, Colo-320, which contains an amplification of the cMYC oncogene.

One aliquot of Colo-320 DNA was labeled by nick translation with FITC-dUTP and a second with Texas red-dUTP nucleotides. Normal human DNA, was used as the reference genome. Two aliquots were labeled similarly to the test genome.

The hybridization array consisted of two target elements. One contained cMYC oncogene sequences, and the other sequences from a region of the human genome (21D7) known to be unamplified in the Colo-320 cell line. DNA from P1 clones (insert length ~80 kb) for these two loci (obtained from the LBL/UCSF Resource for Molecular Cytogenics) was isolated and cut to completion with the restriction enzyme HindIII, resulting in fragments ranging in length from several hundred bp to over 10 kb. One base of the resulting overhang was filled using biotin-dATP, and the DNA was denatured. Thus each single stranded fragment was end labeled with a single biotin. The single stranded fragments corresponding to each clone were reacted with different aliquots of avidin coated controlled pore glass (CPG Inc.) "5 µm particles" (very heterogeneous in size and shape). Thus, one population of particles contained cMYC target sequences, and the other contained 21D7 sequences. Random priming labeling of the single stranded DNA on the particles using FITC-dUTP showed that it was confined to the surface. These large fragments evidently did not substantially penetrate into the pores in the particles.

Two comparative hybridizations were performed to control for potential artifacts due to the differential behavior of labeled probes, and the like.

1) 300 ng of FITC-labeled Colo-320 genomic DNA and 300 ng of Texas-red-labeled normal genomic DNA, and 10 µg of unlabeled $C_o$t-1 DNA were dissolved in 20 µl of hybridization mix to achieve final concentrations of 50% formamide, 2×SSC, and 10% dextran sulfate. This was heated to 70° C to denature the DNA, and 10 µl was added to a small number of particles containing cMYC sequences. The remaining 10 µl was similarly added to a small number of 21D7-containing particles.

2) This hybridization was similar to the first except the fluorochrome labels were reversed. Thus Colo-320 was labeled with Texas-red and normal genomic DNA with FITC. Hybridization proceeded for 36–48 hours at 37° C. and the particles were washed, suspended in fluorescence anti-fade, and mounted on a microscope slide.

Particles were observed with a conventional fluorescence microscope. Hybridization signal was prominent on the surface of the particles (appearing as discrete fluorescence granules). Quantitative CCD camera images of the individual fluorochrome in representative particles were acquired with a digital microscope system with the microscope focused near the equatorial planes of the particles. Images for particles selected to be 10–15 µm in "diameter" are shown in FIG. 1. Due to their size most of each particle was out of focus. The upper panel shows the results when the Colo-320 DNA was labeled with FITC and the normal DNA with Texas red, while the lower panel shows the results when the labeling was reversed. Within each panel the upper row shows Texas red and the lower row shows FITC images. The two columns on the left show particles containing 21D7 target sequences, while the two on the right are particles with cMYC sequences. The exposure for all of the images was 1 sec. and they are displayed without any contrast enhancement or background subtraction.

The upper panel shows that the Texas red labeled normal genomic DNA yielded approximately equal intensities on the two different 21D7 particles and the two cMYC particles. However, the intensity of hybridization of the FITC-labeled Colo-320 DNA to the cMYC particles was substantially higher than to the 21D7 particles. This indicates the presence of more copies of cMYC than 21D7 sequences in the cell line since the ratio of Colo to normal signal on the cMYC particles is substantially higher than on the 21D7 particles. The FITC signal on the cMYC particles formed a ring at the edge of the particle, indicating predominant surface staining.

The lower panel with reverse labelling shows that signal due to the FITC-labeled normal genomic DNA was approximately equal on all of the particles, while the Texas red-labeled Colo-320 DNA yielded a brighter signal on the cMYC particles. Thus the amplification detected was independent of the labeling scheme used.

Quantitative determination of the fluorescence ratios was difficult for these particles because of their thickness and auto fluorescence. However rough estimates indicated that the ratio of the Colo to reference signal on the cMYC particles is more than three times (and perhaps 20 times) larger than the ratio on the 21D7 particles.

The above example is provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method for comparing relative copy number of nucleic acid sequences in a two or more collections of nucleic acid molecules, the method comprising:
   (a) providing a plurality of target elements bound to a solid surface, each target element comprising a target nucleic acid, wherein the target nucleic acid is isolated from a cell nucleus and lacks superstructure of a condensed chromosome;
   (b) contacting the target elements with:
      (I) a first collection of labeled nucleic acid molecules comprising a plurality of first nucleic acid sequences each substantially complementary to a different target nucleic acid, such that the first nucleic acid sequences specifically hybridize to the target nucleic acids under pre-selected hybridization conditions, and
      (ii) at least a second labeled collection of nucleic acid molecules comprising a plurality of second nucleic acid sequences each substantially complementary to a different target nucleic acid, such that the second nucleic acid sequences specifically hybridize to the target nucleic acids under pre-selected hybridization conditions;
      wherein the first and second labels are distinguishable from each other; and
   (c) comparing the amount of binding of the first and second collections of labeled nucleic acid molecules to same target nucleic acid, thereby determining the copy number of at least one of the first nucleic acid sequences relative to the copy number of at least one of the second nucleic acid sequences.

2. The method of claim 1, wherein the target nucleic acids are DNA.

3. The method of claim 1, wherein the target nucleic acids are cDNA.

4. The method of claim 1, wherein the first and second collections of labeled nucleic acids comprise human DNA.

5. The method of claim 1, wherein the target nucleic acids are about 1000 to about 1,000,000 nucleotides in complexity.

6. The method of claim 1, wherein the complexity of the sequence in the first collection of nucleic acids for which relative copy number is determined is less than 1 % of the total complexity of the collection.

7. The method of claim 1, wherein the solid support is a plurality of beads.

8. The method of claim 1, wherein the solid support is glass.

9. The method of claim 1, wherein the first and second labels are fluorescent labels.

10. The method of claim 1, further comprising the step of blocking the hybridization capacity of repetitive sequences in the first and second collections of nucleic acids.

11. The method of claim 10, wherein the first and second collections of nucleic acids are mixed with unlabeled blocking nucleic acids comprising repetitive sequences.

12. The method of claim 11, wherein the unlabeled blocking nucleic acids are Cot-1 DNA.

13. The method of claim 1, wherein the first collection of labeled nucleic acids comprises mRNA or cDNA from a test cell and the second collection of labeled nucleic acids comprises mRNA or cDNA from a reference cell.

14. The method of claim 1, wherein the first collection of labeled nucleic acids is from a test genome and the second collection of labeled nucleic acids is from a normal reference genome.

15. The method of claim 14, wherein the test genome comprises nucleic acids from fetal tissue.

16. The method of claim 14, wherein the test genome comprises nucleic acids from a tumor.

* * * * *